United States Patent [19]

Ali et al.

[11] 4,201,221

[45] May 6, 1980

[54] DIAGNOSTIC TEST FOR ALLERGIC DISORDERS AND KIT THEREFOR

[76] Inventors: Majid Ali, 19 Edgemont Pl., Teaneck, N.J. 07666; Donald J. Nalebuff, 89 Lake Shore Dr., Oakland, N.J. 08106

[21] Appl. No.: 896,296

[22] Filed: Apr. 14, 1978

[51] Int. Cl.$^2$ .......................... A61B 5/00; A61B 6/00; A61B 9/00; A61B 10/00
[52] U.S. Cl. ..................................... 128/630; 128/636
[58] Field of Search ................... 128/2 R; 424/88, 12, 424/8, 9, 2; 23/2 W, 230 B, DIG. 16

[56] References Cited

U.S. PATENT DOCUMENTS 3,410,839  11/1968  Carvalho ................................ 424/88

FOREIGN PATENT DOCUMENTS 7508259  1/1976  Netherlands ........................... 23/230 B

OTHER PUBLICATIONS

"Enzyme-Labeled Antibodies: Preparation and Application for the Localization of Antigens" Nakane et al., Chem. Abstracts, vol. 66, 1967, 27364w.

*Primary Examiner*—Robert W. Michell
*Assistant Examiner*—Thomas J. Wallen
*Attorney, Agent, or Firm*—Ostrolenk, Faber, Gerb & Soffen

[57] ABSTRACT

An immunoglobulin-enzyme bridge technique for the detection of allergen-specific IgE antibodies in biologic fluids of atopic individuals is described.

14 Claims, No Drawings

DIAGNOSTIC TEST FOR ALLERGIC DISORDERS AND KIT THEREFOR

BACKGROUND OF THE INVENTION

In 1966, Ishizaka established that the human allergen reaginic antibodies belong to a distinct class of immunoglobulins, IgE. There followed a decade of remarkable sequence of events. Sensitization of the human and monkey skin to Prausnitz-Kunster reaction by IgE antibodies was demonstrated. It was recognized that the role of IgE is central to the release mechanisms of chemical mediators of anaphylaxis; it mediates immunologic release of histamine from human leucocytes; it primes the human lung tissue for antigen-induced release of histamine and Slow Reacting Substance of Anaphylaxis; it triggers the release of eosinophil chemotactic factor from human lung; and its avidity for attachment, through its Fc portion, to the receptors on the surface of mast cells and basophil granules was shown. It has been inferred that the number and the affinity of IgE antibodies bound to the basophil granulocytes determines the sensitivity of this cell to the allergen, while the histamine release induced by the antigen-antibody reaction on the cell surface is the function of the intracellular enzyme system and cyclic AMP level.

Dating back to the early part of the 20th century, patients with hay fever were treated with injections of incriminated allergens, albeit without understanding the pathologic bases of the disease or the pharmacologic bases for the efficacy of the therapy. Johansoon's observation, in 1967, of augmented levels of serum IgE in atopic patients sparked intense interest in this relationship; individuals with inhalant allergies were found to display seasonal peaks in their serum IgE levels; abatement of allergic symptomatology with immunotherapy was documented. Partial suppression of seasonal peaks following specific immunotherapy was demonstrated and the inter-relationship of levels of IgE and IgG in atopic subjects, and the changes induced by specific immunotherapy have been illuminated.

The advent of the enzyme-labelled antibodies was a major event in the progress of immunochemistry. The immunoperoxidase techniques are now well established investigative tools of a high order of sensitivity and specificity. A measure of their versatility and usefulness is reflected in the diversity of their applications. These immunotracing methods have permitted precise cellular and tissue localization of a very large number of specific antigenic substances and antibodies; notable among these: alpha trypsin in liver, carcinoembryonic antigen in colonic carcinoma, Hepatitis B surface antigen, alpha feto-protein, Herpes simplex virus antigen, and several hormones (thyrocalcitonin, pancreatic, and pituitary). The sensitivity of this method has been shown to surpass that of radioimmunoassay. The localization of light chains and immunoglobulins with these procedures has also been extensively investigated in lymphoid and plasma cells, in bullous dermatosis, in Hodgkin's disease, and in renal diseases where the role of immune mechanism has been invoked.

In 1942, the technique of immunofluorescence for the identification of specific antigenic substances and tissues that escape detection by other histochemical methods was described. Immunofluorescence, however, has continued to pose significant technical difficulties including the requirement of "snap-freezing" of the tissue, the poverty of cellular detail with the use of darkfield condenser, and the distressingly short life of fluorescence.

In 1966, Nakane & Pierce published a report demonstrating that peroxidase could be coupled to an antibody by a simple procedure to produce a stable conjugate. The intact immunological reactivity of such a conjugate was shown to render it eminently suitable for use in immunotracing methods, in a fashion similar to that of fluorescein-labelled antibody. Almost simultaneously, the excellent resolution provided by the oxidation product of 3,3'-diaminobenzidine was put to use in conjunction with peroxidase for histochemical localization purposes. The peroxidase-3,3'-diaminobenzidine system was subsequently employed in the "immunoglobulin-enzyme bridge" technique, in which after the interaction of the specific primary antiserum to the antigen of interest, a second antiserum from a different animal species is applied to provide the "bridge" to the antiperoxidase. The IgG molecule is known to carry two binding sites; it has been inferred that one affords localization to the primary antiserum while the second binds the antiperoxidase, which in turn fixes the peroxidase and its chromogenic substrate to the original antigen under study. The enzyme-chromogenic system has not heretofore been used for the detection of IgE.

Accordingly, it is the object of this invention to provide a method by which the enzyme-chromogenic reagent technique can be applied to the detection of allergen-specific IgE antibodies in biologic fluids of atopic individuals and also to provide a test kit for carrying out the procedure. This and other objects of the invention will become apparent to those skilled in this art from the following detailed description.

SUMMARY OF THE INVENTION

This invention relates to an enzyme-chromogenic technique for the detection of allergen-specific IgE antibodies in biologic fluids of atopic individuals. More particularly, the method involves the contacting of the biologic fluid with a substrate having a bound anti-IgE or allergen thereon, contacting the substrate with non-immune serum of a first animal, contacting the resulting substrate with a second animal's anti-human IgE, contacting the substrate with an enzyme-conjugated first animal anti-second animal IgG, and thereafter contacting the substrate with a chromogenic reagent capable of reacting with the enzyme to develop color. The invention also relates to a test kit for carrying out the method.

DESCRIPTION OF THE INVENTION

The method of the present invention can be performed with any biologic fluids of the patient to be tested. Thus, blood and suitable fluids include nasal, bronchial, middle-ear, gastric, and lachrimal secretions. In the first step of the process, the biologic fluid is contacted with anti-IgE or allergen which is preferably bound to a substrate. Any suitable substrate such as paper, gauze, a swab, etc. can be used. The solid phase media with anti-IgE or allergen fixed thereon are available in commerce, for example, from Pharmacia (in connection with that company's PRIST and RAST tests). The length of contact should be sufficient to permit the reaction between IgE in the biologic fluid and the bound anti-IgE or the allergen and is generally about 0.1–10 hours.

After contacting, the substrate is washed with any suitable inert liquid, such as a phosphate buffered saline having a pH of about 7.6, but this washing step and the other washing steps described below can be eliminated if desired.

In order to eliminate all non-specific binding and to retain only IgE binding, the substrate is next contacted with a non-immune serum from a first animal. Any non-immune serum from a lower animal can be used for this purpose. Suitable animals include the rabbit, monkey, goat, sheep, swine, horse and the like. The contacting time is, as before, that suitable to allow any reactions which are going to occur to take place, and is usually about 1–30 minutes, preferably about 5–15 minutes. The contacting temperature can be any temperature above about 20° C. which does not denature the materials. In accordance with standard incubation techniques, a temperature of about 37° C. is preferred. After the contacting is complete, the substrate is preferably again washed with an inert fluid such as the phosphate buffered saline to remove the non-immune serum from the substrate.

In the next step of the instant method, the substrate is contacted with anti-human IgE of a second animal. The anti-human IgE can be obtained from any of the lower animals mentioned previously but it is necessary that the second animal be different from that of the first animal. The animals must be different in order to preserve immunologic specificity of the test procedure. The contacting time is, as before, that sufficient to permit reactions to take place, generally 5–30 minutes, and preferably about 1–20 minutes at a temperature above 20° C. which does not denature the materials. Again, a temperature of about 37° C. is preferred. After the contacting step is complete, the substrate is again washed with an inert fluid.

In the next step of the present method, the substrate is contacted with a secondary antiserum which is an enzyme conjugated serum of said first animal which is anti-IgG of said second animal. Enzyme conjugated antisera are known in the art and any enzyme which reacts with the chromogenic system employed in the subsequent step can be utilized. The preferred enzyme is peroxidase although other enzymes such as alkaline phosphatase, and the like can also be used. The contacting time is again that sufficient to allow any reactions to take place and is generally about 0.1–2 hours, preferably about 0.25–0.75 hour. Any temperature above 20° C. can be employed and this step is preferably effected at ambient temperature. Following this step, the substrate is again washed with an inert fluid.

It has been found that the anti-human IgE of the second animal and the enzyme conjugated anti-second animal IgG of the first animal must be diluted within a particular range in an inert carrier in order to achieve the results of this invention. The carrier must be inert to the system and the reagents being utilized and any material meeting this qualification can be employed. It is preferred to employ pharmaceutically acceptable carriers and the phosphate buffered saline used in the washing steps has been found to be particularly suitable. The dilution of the antisera must be greater than 1:5 and less than 1:1000. Preferably the dilution is greater than 1:50 and less than 1:250 and best results have been obtained with dilutions of about 1:100–1:200.

In the final step of the instant process, the substrate is contacted with a chromogenic system which will react with the conjugated enzyme to develop color. Any chromogenic reagent which reacts with the conjugated enzyme to develop color can be employed in this step. A chromogenic reagent containing hydrogen peroxide and 3,3'-diaminobenzidine is a popular system when the enzyme is peroxidase and it is preferred to use this system in the present invention. Other chromogenic systems such as alpha-naphthol pyronin, and the like, can also be used. The reagent is conveniently employed in the form of a solution in an inert carrier and the phosphate buffered saline is particularly suitable as the solvent. The substrate is contacted with the chromogenic reagent for a time sufficient to allow color to develop which is usually about 0.1–1 hour and preferably about 0.1–0.25 hour. The contacting temperature is preferably ambient.

In order to demonstrate the method of the present invention, the following experiments were carried out.

Sera from 20 allergic patients and 10 non-allergic subjects (as control) were tested for the presence of total and allergen specific IgE antibodies using Pharmacia's PRIST test cyanogenbromide activated disc and RAST disc carrying specific allergens. The discs were thereafter washed with phosphate buffered saline (pH about 7.6) and then contacted with a rabbit non-immune serum for 10 minutes at 37° C. in a humidified chamber. The discs were then washed with an additional quantity of the buffered saline and then contacted with the primary antiserum (goat anti-human IgE) for 15 minutes at 37° C. in a humidified chamber. The discs were then again washed with the buffered saline for 10 minutes and then contacted with the secondary antiserum (peroxidase conjugated rabbit anti-goat IgG) for 30 minutes at room temperature. Thereafter the discs were washed again with the buffered saline for 10 minutes and then contacted with a freshly prepared peroxide-diaminobenzidine solution for 10 minutes at room temperature under a foil cover. The chromogenic solution had been prepared by adding 0.1 ml of 3 percent hydrogen peroxide to 100 ml of the phosphate buffered saline containing 50 mg of 3,3'-diaminobenzidine.

The controls for human IgE specificity were established by carrying discs under study through all of the steps of the procedure except for application of the primary antiseum.

Intense brown staining was observed on the test discs. The control discs from non-allergic patients displayed a faint brownish hue which was characterized as a negative result. The control discs unexposed to non-immune antiserum but exposed to the peroxidase conjugate and histochemical reagents displayed absence of the brown reaction product. The brown staining is furnished by precipitation of a brown insoluble polymer of 3,3'-diaminobenzidine, which is oxidized by nascent oxygen released from hydrogen peroxide under the catalytic influence of peroxidase. The enzyme, having been bound previously to IgE antibodies on discs by the double antibody technique, produced the brown color. The colors did not fade in storage and were therefore of value as permanent records. The depth of the brown color can be used to estimate the degree of sensitivity to the allergens.

In accordance with the present invention, a package containing the materials utilized to carry out the instant method is also provided. The package contains in ampules or other suitable containers, anti-IgE or allergen preferably bound to a solid substrate, a non-immune serum from a first animal, an anti-human IgE serum from a second animal, an enzyme conjugated anti-second animal IgG of the first animal, and a chromogenic reagent capable of reacting with the enzyme to develop color. The package also preferably contains a supply of the inert washing fluid such as, for example, the phosphate buffered saline.

Various changes and modifications can be made in the method and product of this invention without departing from the spirit and scope thereof. For example, the sequence of contact with the various antibodies can be reversed if desired or an anti-enzyme antibody can be employed. The various embodiments described herein were for the purpose of further illustrating the invention but were not intended to limit it.

We claim:

1. A method of determining sensitivity of a patient to allergens comprising contacting a biologic fluid of the patient with anti-IgE or allergen; contacting the reaction product with a non-immune serum of a first animal; contacting the resulting reaction product with (a) a second animal anti-human IgE diluted in an inert carrier to greater than 1:5 and less than 1:1000 or (b) an enzyme conjugated first animal anti-second animal IgG diluted in an inert carrier to greater than 1:5 and less than 1:1000, followed by contacting the reaction product thus formed with the other of said (a) or (b); and thereafter contacting the reaction product thus formed with a chromogenic reagent capable of reacting with the enzyme to develop color.

2. The method of claim 1 wherein said anti-IgE or allergen is bound to a substrate and the substrate is contacted in the subsequent steps.

3. The method of claim 2 wherein said dilutions are greater than 1:50 and less than 1:250.

4. The method of claim 3 wherein said dilutions are about 1:100–1:200.

5. The method of claim 2 wherein said enzyme is peroxidase.

6. The method of claim 5 wherein said chromogenic reagent is a solution of hydrogen peroxide and 3,3'-diaminobenzidine.

7. The method of claim 1 wherein contact with (a) is effected before contact with (b).

8. A package containing (a) anti-IgE or allergen; (b) non-immune serum from a first animal; (c) anti-human IgE from a second animal diluted in an inert carrier to greater than 1:5 and less than 1:1000; (d) an enzyme conjugated anti-second animal IgG of said first animal diluted in an inert carrier to greater than 1:5 and less than 1:1000; and (e) a chromogenic reagent capable of reacting with said enzyme to develop color.

9. The package of claim 8 wherein said dilutions are greater than 1:50 and less than 1:250.

10. The package of claim 9 wherein said dilutions are about 1:100–1:200.

11. The package of claim 8 wherein said carrier is phosphate buffered saline.

12. The package of claim 8 wherein said enzyme is peroxidase.

13. The package of claim 12 wherein said chromogenic reagent is a solution of hydrogen peroxide and 3,3'-diaminobenzidine.

14. The package of claim 8 wherein said anti-IgE or allergen is bound to a substrate.